(12) United States Patent
Tyber et al.

(10) Patent No.: US 8,182,539 B2
(45) Date of Patent: May 22, 2012

(54) DYNAMIC INTERBODY WITH MOTION CONTROL MECHANISMS

(75) Inventors: Jeffrey Tyber, Bethlehem, PA (US); Matthew Kovach, Steamboat Springs, CO (US); Larry Pijanowski, Red Hill, PA (US)

(73) Assignee: Aesculap Implant Systems, LLC, Center Valley, PA (US)

( * ) Notice: Subject to any disclaimer, the term of this patent is extended or adjusted under 35 U.S.C. 154(b) by 606 days.

(21) Appl. No.: 12/256,713

(22) Filed: Oct. 23, 2008

(65) Prior Publication Data

US 2010/0106249 A1    Apr. 29, 2010

(51) Int. Cl.
*A61F 2/44*    (2006.01)
(52) U.S. Cl. .................................................. 623/17.16
(58) Field of Classification Search ..... 623/17.11–17.16
See application file for complete search history.

(56) References Cited

U.S. PATENT DOCUMENTS

| | | | |
|---|---|---|---|
| 4,904,261 A | 2/1990 | Dove et al. | |
| 5,827,328 A | 10/1998 | Buttermann | |
| 6,206,881 B1 | 3/2001 | Frigg et al. | |
| 6,660,038 B2 | 12/2003 | Boyer | |
| 6,758,863 B2 | 7/2004 | Estes et al. | |
| 6,984,234 B2 | 1/2006 | Bray | |
| 7,041,135 B2* | 5/2006 | Michelson | 623/17.11 |
| 7,077,864 B2 | 7/2006 | Byrd, III et al. | |
| 7,112,222 B2 | 9/2006 | Fraser et al. | |
| 7,232,464 B2 | 6/2007 | Mathieu et al. | |
| 2005/0125063 A1 | 6/2005 | Matge | |
| 2006/0030851 A1 | 2/2006 | Bray | |
| 2006/0085071 A1* | 4/2006 | Lechmann et al. | 623/17.11 |
| 2007/0093901 A1 | 4/2007 | Grotz | |
| 2009/0210064 A1* | 8/2009 | Lechmann et al. | 623/17.16 |

FOREIGN PATENT DOCUMENTS

| | | |
|---|---|---|
| WO | WO 2005/069106 | 7/2005 |
| WO | WO 2006/037621 | 4/2006 |
| WO | WO 2006/040063 | 4/2006 |
| WO | WO 2006/108114 | 10/2006 |
| WO | WO 2007/115208 | 10/2007 |

OTHER PUBLICATIONS

Pending U.S. Appl. No. 12/015,276, filed Jan. 16, 2008.
Pending U.S. Appl. No. 12/019,760, filed Jan. 25, 2008.
Office Action for U.S. Appl. No. 12/019,760, mailed Jun. 8, 2011.

* cited by examiner

*Primary Examiner* — Eduardo C Robert
*Assistant Examiner* — Steven Cotroneo
(74) *Attorney, Agent, or Firm* — RatnerPrestia

(57) ABSTRACT

An intervertebral implant includes a body for insertion between adjacent vertebrae, and one or more anchors extending from the body for securing the body between the vertebrae. A linear motion control mechanism is mounted in the body and operable to limit linear translation of the anchor(s) relative to the body. Also, a pivot control mechanism in the body operates to limit pivot motion of the anchor(s) relative to the body. The linear and pivot control mechanisms are configured in various arrangements and embodiments exhibiting adjustable dynamic settings, allowing a single implant to provide various types of dynamic fixation with ranges of motion that permit loads to transfer to graft material contained in the disk space.

15 Claims, 7 Drawing Sheets

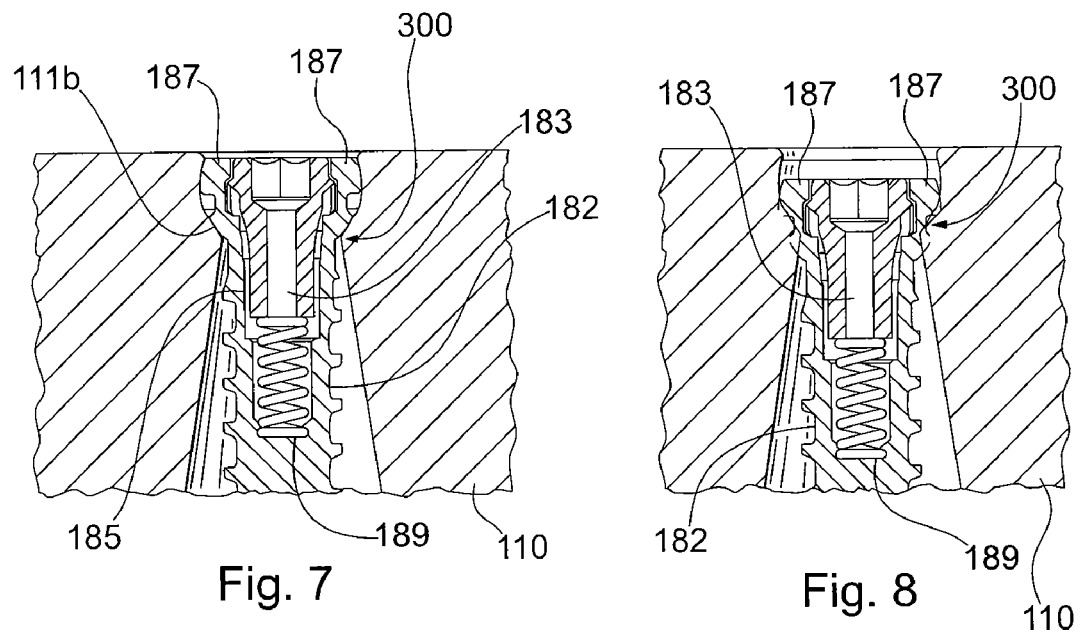
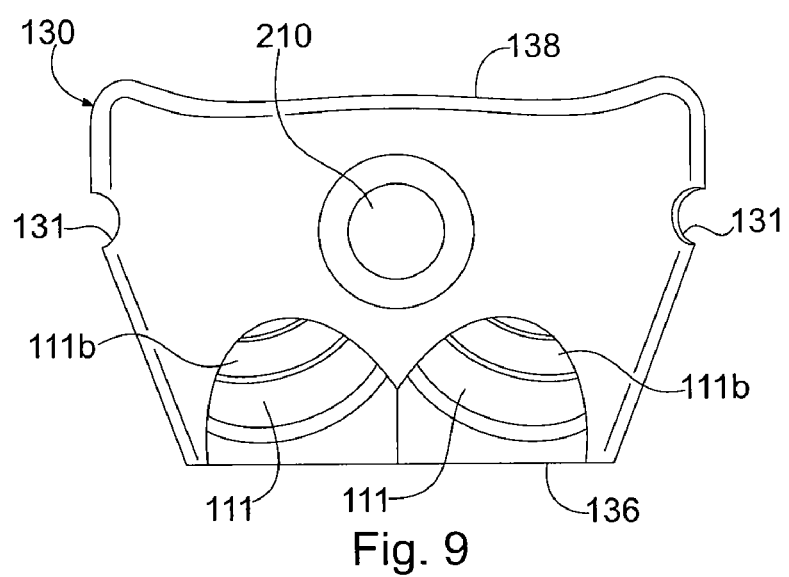

DYNAMIC INTERBODY WITH MOTION CONTROL MECHANISMS

FIELD OF THE INVENTION

The present invention relates generally to spinal fusion techniques, and more specifically an anterior lumbar interbody used in spinal fusion which may be changed intraoperatively between a constrained setting, a semi-constrained setting, a dynamic setting, or a combination of such settings, each setting allowing fixation elements, such as anchor screws, to move through a limited range of motion and control the transfer of load to the implant.

BACKGROUND OF THE INVENTION

In spinal fusion, two or more vertebrae are joined by a fusion material placed between the vertebrae. Once fusion is complete, the fusion material immobilizes the vertebrae. Spinal fusion is used primarily to treat pain caused by abnormal motion of the vertebrae. Anterior lumbar interbody fusion (ALIF) is a spinal fusion technique that can be used for treating degenerative discs from an anterior approach. The anterior approach allows access to the interbody space with minimal damage to the posterior musculature, while allowing full decompression of the diseased disc. During an ALIF procedure, an interbody device is inserted within the intervertebral body space. In many cases, the interbody is a rigid body with a central opening. The opening may be filled with bone graft material, such as an autograft or allograft material. The objective of interbody fusion is to fuse the central graft material to the cranial and caudal endplates, creating a rigid boney union between motion segments.

Many known interbody designs utilize a rigidly constrained fixation, in which anchors, such as bone screws, are rigidly set in the interbodies and in the bone. The anchor screws are constrained in the sense that they are fixed and cannot move relative to the interbody. This rigid construct is intended to provide stability to the implant. At the same time, a rigid construct will stress-shield the graft material. That is, the interbodies and anchor screws form a rigid frame around the graft material that absorbs axial loads from the vertebrae being fused together, thereby shielding the graft material from axial load.

SUMMARY OF THE INVENTION

In a first exemplary embodiment of the invention, an intervertebral implant includes a body for insertion between adjacent vertebrae, and an anchor extending from the body for securing the body between the vertebrae. A linear motion control mechanism is mounted in the body to limit linear translation of the anchor relative to the body. Also, a pivot control mechanism in the body to limits pivot motion of the anchor relative to the body.

In a second exemplary embodiment of the invention, an intervertebral implant includes a body for insertion between adjacent vertebrae, and an anchor extending from the body for securing the body between the vertebrae. The anchor includes a head that pivots relative to the body. A linear motion control mechanism is connected with the head of the anchor and operable to limit linear translation of the anchor relative to the body. A pivot control mechanism also engages the head of the anchor and operates to limit pivot motion of the anchor relative to the body.

In a third exemplary embodiment of the invention, an intervertebral implant includes a body for insertion between adjacent vertebrae. An anchor extends from the body for securing the body between the vertebrae. The anchor includes a head that is pivotable relative to the body. A linear motion lock engages the head of the anchor to limit linear translation of the anchor relative to the body. A pivot motion lock also engages the head of the anchor to limit pivot motion of the anchor relative to the body.

BRIEF DESCRIPTION OF THE DRAWINGS

The foregoing summary and the following description will be better understood in conjunction with the drawing figures, of which:

FIG. 7 is a cross section view of a body component and anchor element used in the implant of FIG. 1, with the body component truncated for clarity, showing the anchor element in a first locking condition;

FIG. 8 is a cross section view of a body component and anchor element used in the implant of FIG. 1, with the body component truncated for clarity, showing the anchor element in a second locking condition;

FIG. 9 is a bottom view of a carrier component of the implant of FIG. 1;

DETAILED DESCRIPTION OF THE PREFERRED EMBODIMENTS OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

Applicants have observed a number of problems and drawbacks associated with interbody cages that use rigidly constrained fixation members, such as bone screws that are fixed in angulation and position relative to the interbody. Interbody cages are capable of subsiding into endplates of adjacent vertebra by as much as 6 mm. When fixation screws are rigidly constrained in the interbody, the fixation screws provide resistance against subsidence of the endplates, absorbing axial load during settling. This creates a number of concerns. First, some screws are not optimal for bearing all the load caused by settlement, and may be compromised if the loads are excessive. Second, because the fixation screws absorb the loads that occur from subsidence, the fixation screws and interbody stress-shield the bone graft material. Wolff's Law recognizes that bone material is a living structure that adapts to loads and remodels itself over time to accommodate the loads. Bone material grows and becomes stronger in response to increased stresses. If bone graft material is shielded from loads that occur during settlement, bone growth will be inhibited and fusion will not occur properly. Subsidence has been linked to pseudoarthrodesis and non-union of the fusion site. Accordingly, the temptation to use a rigid construct can have the unintended result of hampering fusion.

The fusion interbody assemblies of the present invention improve upon prior approaches by addressing subsidence and settling of the endplates while limiting stress-shielding of the graft material. The various embodiments of the present invention allow proper load distribution to the bone graft material during subsidence, while still utilizing fixation members like bone screws within the disc space. This is accomplished by allowing fixation to occur over time as a dynamic process in response to subsidence and settling. Rather than absorb loads that occur during subsidence, the bone screws are permitted to translate and/or pivot with respect to the interbody as the implant subsides. This allows the subsidence loads to be transferred to the bone graft material, rather than be absorbed by the bone screws. To accomplish this, the embodiments include translation mechanisms that allow the screws to translate in a linear direction, pivot, or both, in response to subsidence and settlement, while maintaining the screws firmly anchored in the implant. The assemblies also include one or motion control mechanisms that allow selective operation and adjustment of the translation mechanisms for each screw.

Figure 1:
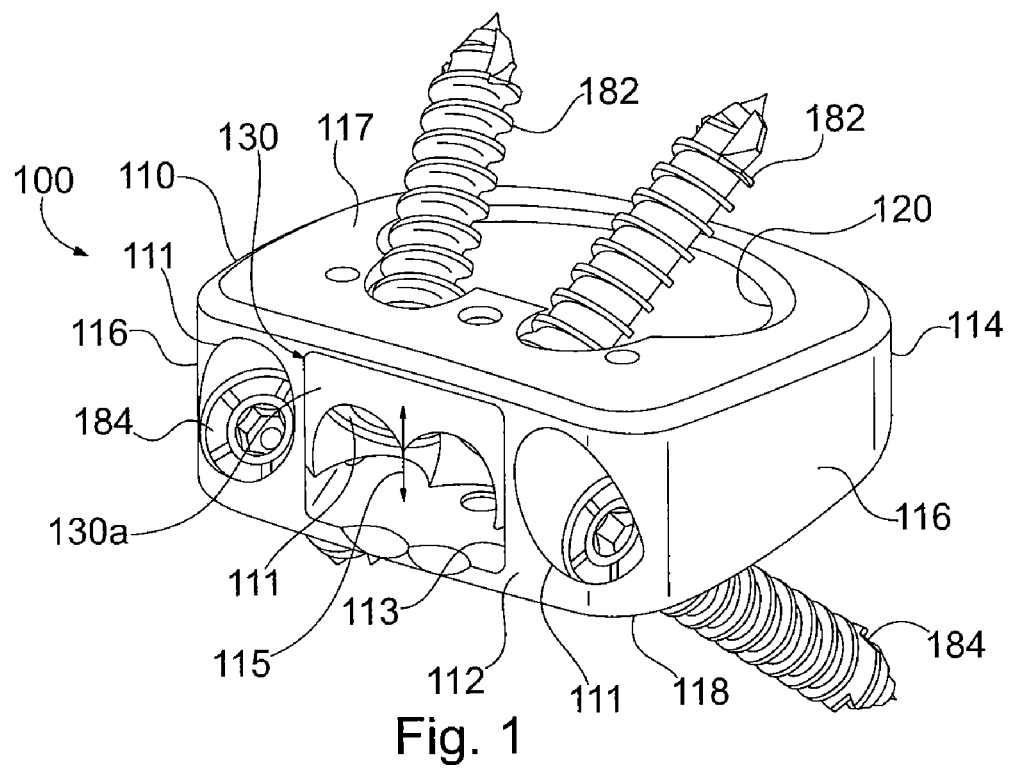
FIG. 1 is a perspective view of an intervertebral implant in accordance with one exemplary embodiment of the invention.

Referring now to FIG. 1, an interbody assembly 100 is shown in accordance with one exemplary embodiment of the invention. Interbody assemblies in accordance with the present invention may include a variety of body and anchor configurations. Interbody assembly 100 includes a rigid body 110 and a plurality of bone screws that are passed through the body. For purposes of this description, the terms "anterior", "posterior", "superior" and "inferior" describe the position of surfaces or features relative to the anatomy. The term "anterior" refers to features having a to relative position toward the front side of a spine, and "posterior" refers to features having a relative position toward the rear side of the spine. The term "superior" refers to features having a relative position above other features, in the cranial direction, and the term "inferior" refers to features having a relative position below other features in a caudal direction.

Body 110 has an anterior wall 112 and a posterior wall 114 that is generally parallel to the anterior wall. Anterior wall 112 has a larger external surface area than posterior wall 114. Anterior and posterior walls 112, 114 are joined by a pair of lateral side walls 116 that extend generally parallel to one another. A superior end wall 117 and an inferior end wall 118 extend in a non-parallel manner between anterior and posterior side walls 112, 114. Superior and inferior end walls 116, 118 taper or converge toward one another as they extend toward posterior side wall 114, forming a wedge-shaped structure. The anterior, posterior and lateral side walls, 112, 114, and 116 surround a central opening 120 that forms a space for fusion material, such as a bone graft or bone graft substitute.

Interbody assembly 100 includes a plurality of screw holes 111 for receiving anchoring screws. A pair of inner screws 180 extend through anterior side wall 112 and project out of superior end wall 117. A pair of outer screws 184 extend through anterior side wall 112 and project out of inferior end wall 118. Inner and outer screws 182, 184 each have rounded heads 182a, 184a and threaded shanks 182b, 184b, seen more clearly in FIG. 3. Heads 182a, 184a have rounded configurations that allow the screws to assume a polyaxial range of motion, as will be described below. Shanks 182b, 184b have external threads for anchoring the screws into vertebral bodies above and below the disk space.

Anterior wall 112 includes a sliding block or carrier 130 that carries inner screws 182. Carrier 130 allows screw heads 182a to translate in a linear direction relative to body 110 during subsidence of the end plates after the interbody assembly 100 is inserted into a disc space. The direction of translation is illustrated by double-ended arrow 115 in FIG. 1. Carrier 130 is slidably arranged in a receptacle 113 formed in the anterior side wall 112 of body 110. An anterior face 130a on carrier 130 is substantially flush with anterior side wall 112 of body 110. Two screw holes 111 extend through carrier 130 and open out into the central opening 120. In this arrangement, inner screws 182 can translate linearly in response to linear displacement of carrier 130.

Figure 2:
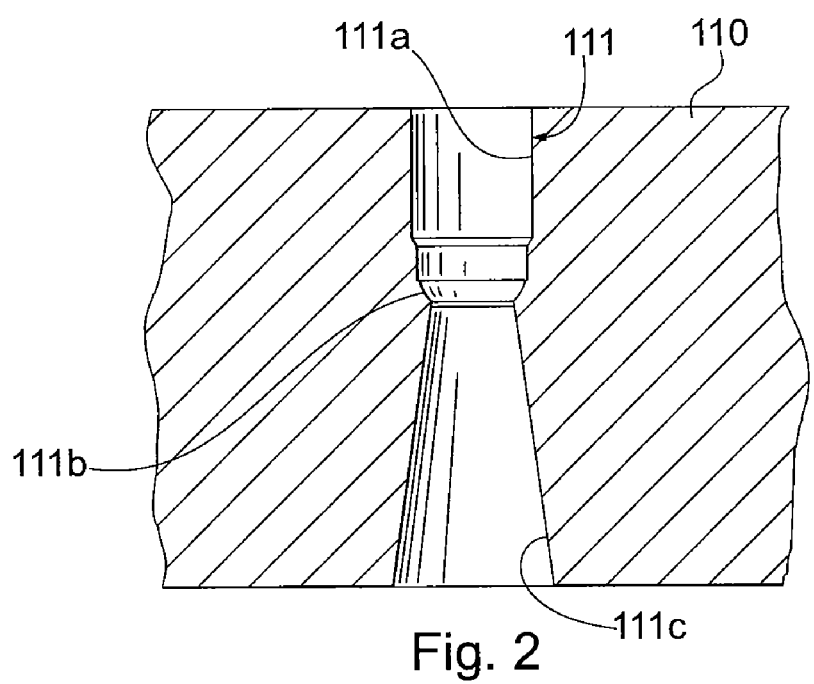
FIG. 2 is a truncated cross section view of a component of the intervertebral implant of FIG. 1, showing a hole configuration.

Referring now to FIG. 2, the cross-sectional profile of one of the screw holes 111 is shown. Hole 111 includes a substantially cylindrical section 111a and a rounded seat 111b. Cylindrical section 111a allows for insertion of a screw into the hole and is large enough to receive screw heads 182a, 184a. Screw heads 182a, 184a have rounded surfaces that conform to the curvature of rounded seat 111b. Screw hole 111 further includes a cone-shaped section 111c having a diameter that gradually increases as the cone-shaped section extends away from seat 111b. In this arrangement, screws 182, 184 are permitted to rotate about their longitudinal axis, as well as pivot and rotate about different axes, in a polyaxial range of motion. As will be described below, this polyaxial range of motion permits the screws to pivot relative to the body, allowing the superior and/or inferior end plates of the vertebrae to subside in a non-linear direction relative to the implant and transfer load to the graft material.

Carrier 130 and the polyaxial screw hole arrangements provide two motion mechanisms, each mechanism providing a different type of motion. There is "linear motion", in which the screw heads translate in a linear direction relative to the interbody, and "pivot motion", in which the screw shanks are permitted to move through a polyaxial range of motion. Screw hole sections 111c allow each screw to move in a cone-shaped range of polyaxial motion during pivot motion. Linear motion and pivot motion can be independently controlled and limited by separate motion control mechanisms to customize the dynamic behavior of the screws relative to the implant during subsidence.

Figure 3:
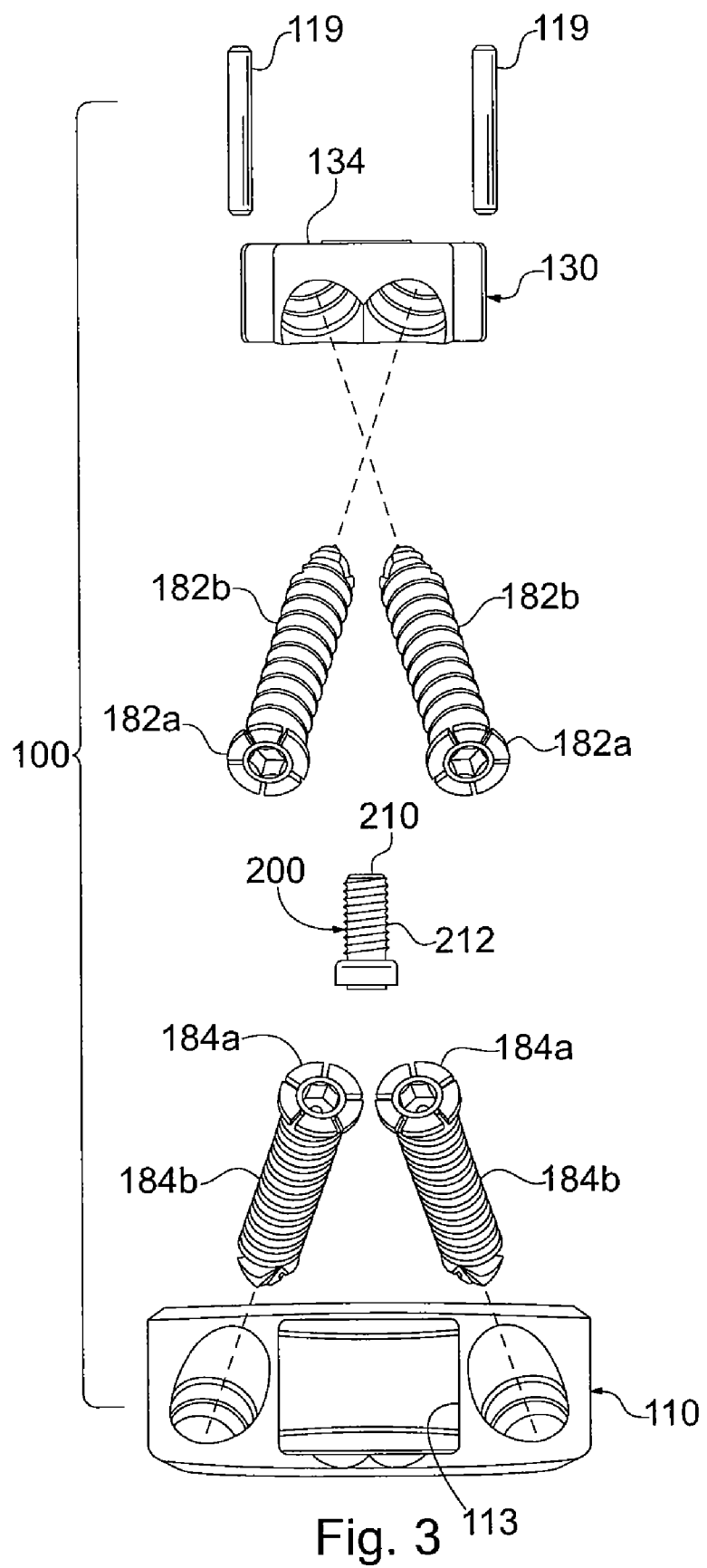
FIG. 3 is an exploded front elevation view of components of the implant of FIG. 1.
Figure 4:
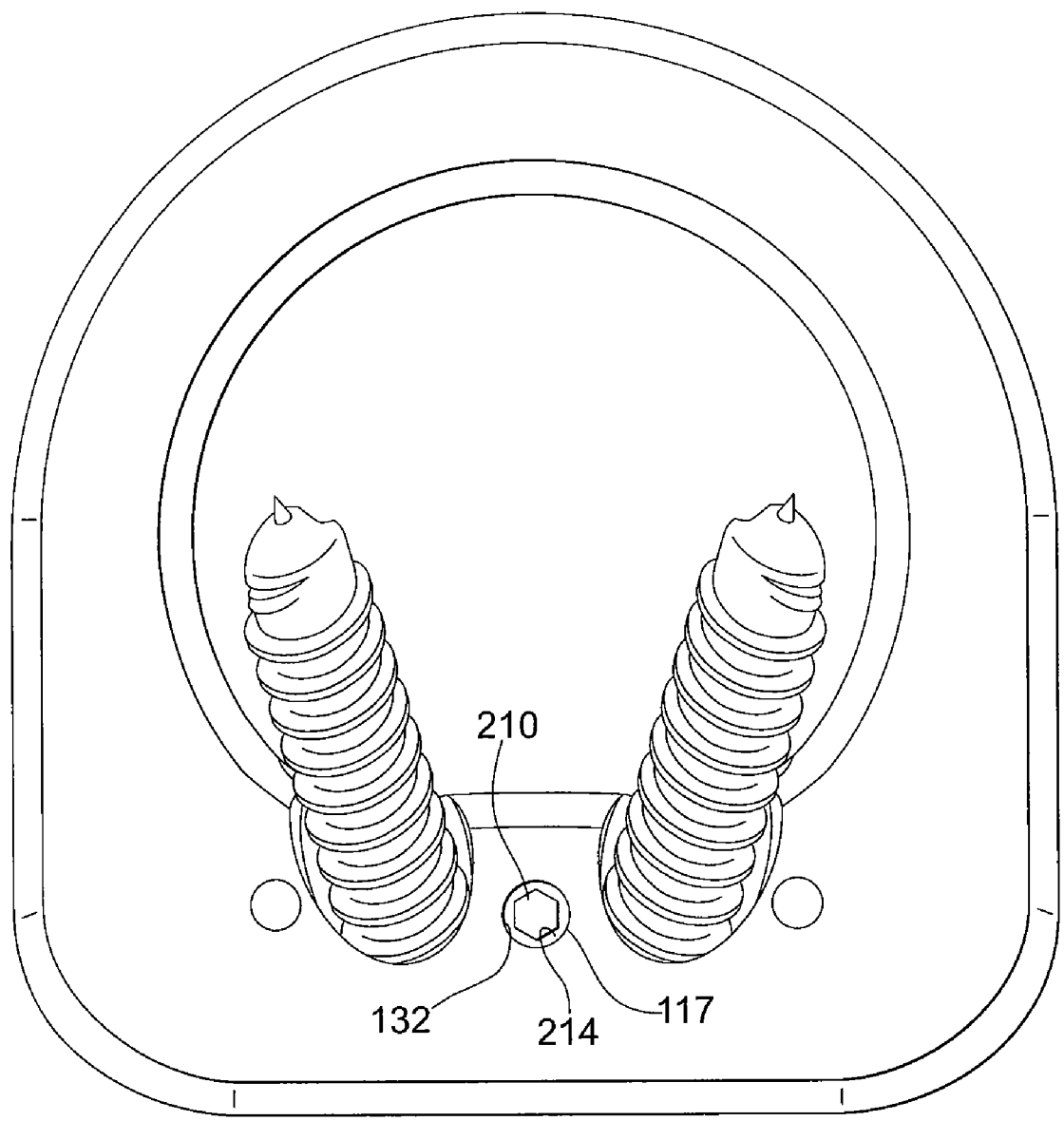
FIG. 4 is a top view of the implant of FIG. 1.

Referring to FIGS. 3 and 4, assembly 100 includes a linear motion control mechanism 200. Linear motion control mechanism 200 includes a retractable lock element 210 that extends from an inferior side of carrier 130. Lock element 210 is extendable and retractable from a bore 132 inside carrier 130. An external thread 212 on lock element 210 engages an internal thread 134 in bore 132. In this arrangement, lock element 210 is axially displaceable in bore 132 in response to rotational force applied to the lock element. The relative position of lock element 210 is therefore adjustable.

Figure 5:
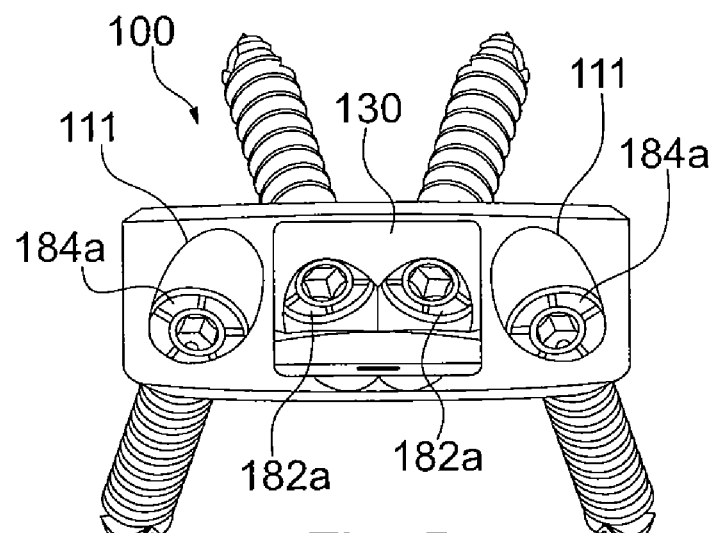
FIG. 5 is a front elevation view of the implant of FIG. 1 configured in a first setting.
Figure 6:
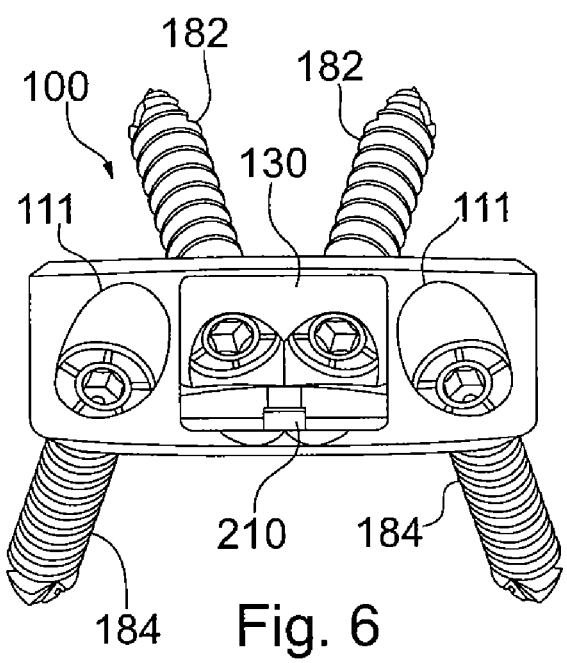
FIG. 6 is a front elevation view of the implant of FIG. 1 configured in a second setting.

Referring to FIG. 4, the top of lock element 210 has a hexagonal socket 214, which is exposed through a portal 117 in body 110. Portal 117 provides access for a hex wrench or other torque applying instrument to engage lock element 210. Lock element 210 is axially displaceable between a retracted condition, shown in FIG. 5, in which the lock element is concealed inside carrier 130, and an extended position, shown in FIG. 6, in which the lock element is partially visible. In the retracted position, lock element 210 is contained entirely in carrier 130, allowing the carrier to move linearly in receptacle 113. In the extended position, lock element 210 projects beneath the bottom of carrier 130 into engagement with a bottom surface of receptacle 113, preventing the carrier from moving in the receptacle.

Thus far, implant body 100 and carrier 130 have been shown and described with inner screws 182 extending into the superior vertebrae, and outer screws 184 extending into the inferior vertebrae. Other orientations for the body, carrier and screws are envisioned as suitable alternative embodiments within the scope of the invention. For example, the carrier 130 and inner screws 182 in FIG. 1 could be inverted in an alternative embodiment so that the inner screws are mounted in an inferior endplate. The outer screw hole configurations could likewise be reoriented so that outer screws 184 are mounted in a superior endplate.

Referring to FIGS. 7 and 8, assembly 100 further includes a pivot motion control mechanism 300 that operates independently of linear motion control mechanism 200. Pivot control mechanism 300 is embodied at the interfaces between the screws 182, 184 and the seats 111b of screw holes 111. The implant body 110 and carrier 130, or at least the portions of the body and carrier forming the seats 111b, are made of a plastically deformable material. In a preferred embodiment, body 110 and carrier 210 are formed of polyetheretherketone, or PEEK, which provides suitable plastic deformation properties. Other materials can also be used with satisfactory results, including but not limited to Titanium or a combination of PEEK and Titanium.

The screw heads 182a, 184a are adjustable between two locking positions in the screw holes 111. In the first locking position, shown in FIG. 7, a screw head 182a (or 184a) is secured in a screw hole to a first depth, where the head slidably engages the curvature of the seat in response to lateral force on the screw shank. The head is essentially captured within rounded seat portion 111b, where it is free to pivot through polyaxial motion. In the second locking position, shown in FIG. 8, the screw head is advanced further into the screw hole 111, beyond the original seat configuration. The cross section of hole 111 includes a constriction 111d at the base of seat portion 111b. The constriction 111d is smaller than the diameter of the screw. Constriction 111d is configured to plastically deform to allow the screw head to penetrate further into the hole. Preferably, the exterior of the anchor elements include indentations or voids that allow material to flow into and around the anchor heads during plastic deformation. In FIGS. 7 and 8, screw head 182a includes a groove 182c surrounding the head. PEEK material along hole 111 flows into groove 182c during plastic deformation, trapping the head in a second locking position. In the second locking position, the screw head is immobilized against rotation and pivot motion relative to the plate, such that the screw cannot move in any direction relative to the plate.

The two independent motion control mechanisms 200, 300 provide a number of different settings to control how each screw individually, and the screws collectively, move relative to implant body 110 during subsidence. The settings determine the range of motion of the vertebrae around the implant as the vertebrae subside, and to what extent stresses are shielded around implant body 110. Screw motion may be controlled to permit the superior vertebrae to move linearly, with no pivot motion relative to the implant body. Alternatively, screw motion may be controlled to permit pivot motion of both vertebra, with no linear motion. These two types of motion can be combined with one another in different ways to control the dynamic behavior of the implant during subsidence, as explained below.

Motion settings can be selected prior to implantation, or intraoperatively, to adjust the extent to which vertebrae can subside and bear against the implant. The two control mechanisms 200, 300 may be set to provide axial translation only, pivot motion only, a combination of axial translation and pivot motion, or no relative motion. The implants in accordance with the invention are operable in three basic modes: (1) "dynamic fixation", which allows the screws to translate in a linear direction as well as pivot relative to the body, (2) "semi-constrained fixation", in which the screws are not allowed to translate in a linear direction but can pivot relative to the body, and (3) "constrained fixation", in which the screws can neither translate nor pivot relative to the body. When implant 100 is set to dynamic fixation, linear motion control mechanism 200 is unlocked to allow carrier 130 to move, and all screw heads 182a, 184a are pivotable in the first locking condition in the holes 111. In semi-constrained fixation, linear motion control mechanism 200 is locked to prevent carrier 130 from moving, while all screw heads 182a, 184a are still pivotable in the first locking condition in the holes 111. In constrained fixation, linear motion control mechanism 200 is locked to prevent carrier 130 from moving, and all screw heads 182a, 184a are immobilized in the second locking condition in the holes 111, so that the screws cannot move in any direction relative to the interbody 110.

In addition to the three basic modes, the control mechanisms may be set in a number of hybrid states, where selected screws are set in one of the three basic modes, and other screws are set in another of the three basic modes. For example, inner screws 182 may be advanced to the first locking position in carrier 130, with the lock element 210 in the retracted position, so as to allow the inner screws to translate and pivot relative to the body as they would in dynamic fixation. At the same time, outer screws 184 may be advanced to the second locking position corresponding to constrained fixation, preventing the outer screws from moving relative to implant body 110. This combination of settings provides for different ranges of motion for the superior and inferior vertebrae relative to the body. Other combinations of settings may be used in accordance with the invention to customize the range of motion. The dynamic behavior of each screw may be set to facilitate a symmetrical range of motion of the vertebra, or concentrate movement around one particular area or side of the implant.

Screws 182, 184 preferably include their own internal locking mechanisms to more securely mount the screw heads into the screw holes 111. A number of self-locking bone screws can be used, such as the type used with the ABC2 Anterior Cervical Plating System manufactured by Aesculap Implant Systems, Inc. Screw heads 182a, 184a include a central bore 185 and a plurality of radially expandable segments 187 surrounding the bore. Bore 185 contains a plug 183 that engages a compression spring 189 mounted inside the screw. Plug 183 is biased upwardly toward the screw head by spring 189, so that the plug engages the segments 187 and displaces them outwardly. When the screw is being driven into bone, the plug is pushed down into the screw against the spring by the screw driver, allowing the segments 187 to radially converge inwardly. This reduces the size of screw head temporarily to allow the screw to pass into narrower sections of the hole. When the driving tool is removed, plug 183 is released and returns into its original position under the bias of the spring. As the plug returns to its normal position, the plug pushes segments 187 radially outwardly. The plug 183 forces the segments 187 outwardly into a frictional engagement with the seat 111b to stabilize, but not necessarily lock, the position of the screw head against the seat.

Referring now to FIG. 9, a bottom view of carrier 130 is shown. Carrier 130 has a narrow anterior face 136 and a wider posterior face 138. The wider face 138 is contiguous with the central opening 120 in body 110 when the carrier and body are assembled. The width of carrier 130 tapers from a narrower width at the anterior face 136 to a larger width at the posterior face 138, forming a wedge-shaped profile. The wedge shape of carrier 130 minimizes the risk of the carrier being dislodged anteriorly out of the implant body. The bottom of locking element 210 is shown substantially centered in carrier 130.

Carrier 130 is secured in receptacle 113 by a pair of rails 119, which are shown in detail in FIG. 3. Rails 119 provide a locking mechanism to lock the carrier in receptacle 113. Carrier 130 is slidably displaceable on rails 119, such that the rails provide a track that controls linear motion of the carrier. Preferably, rails 119 are formed of radio opaque material so that the rails can serve as radio markers under imaging. Carrier 130 includes a pair of circular grooves 131, shown best in FIG. 9, that facilitate a locking connection with rails 119.

The ability to adjust the assembly between different dynamic settings, e.g. dynamic, semi-constrained, constrained, and hybrid conditions, provides a versatile implant that provides surgeons and patients with more options in a single implant. The surgeon is not compelled to choose between different implants, screws and/or screw hole profiles to establish a desired range of motion. Because of this versatility, assemblies of the present invention remove the inherent uncertainties and risks associated with deciding between different implants, screws and hole configurations by offering a number of possible dynamic settings in a single assembly. Dynamic characteristics of the implant assemblies can be selected before the assemblies are implanted, or selected or adjusted after the assemblies are in place. The different dynamic settings of the implant assemblies can all be achieved using one common implant body, hole configuration and screw type.

Pivot motion can be adjusted for each individual screw. Instead of physically removing and replacing each screw, pivot motion is selected or changed by applying different amounts of torque on the screw. Each screw is installed and driven against a rounded seat portion by applying torque on the screw head. The plastically deformable seat portions in screw holes 111 are configured to yield under a threshold force. Any force that is less than the threshold value will drive the screw head against the rounded seat portion in the first locking position, at which point the head will advance no further in the screw hole. Force applied to the screw in excess of the threshold limit will advance the screw head further and plastically deform the seat until the screw head reaches the second locking position.

A plastically deformable interbody goes against traditional approaches that subscribe to the use of a very rigid body material for maintaining proper disk space height. If the interbody has sufficient plasticity to deform under load, the disc space can contract, which can be undesirable. The implant assemblies of the present invention combine internal plasticity inside the screw holes, which allows small amounts of controlled screw movement to lock the screw, with an overall rigid assembly. This provides a controlled movement of the screws for the desired purposes of locking the screw heads into the body, without substantial plastic deformation on the exterior of the body, creating a controlled dynamic that is not expected or desired in prior approaches.

The screws preferably include an internal locking mechanism, as noted above. The internal locking mechanism, combined with the plastically deformable seat surfaces and the screw threads, provide up to three levels of security for each screw that prevent the screw from reversing out of the screw hole. The first level of security is provided by the threads of the screw shank, which engage bone to stabilize the screw in the implanted condition. The second level of security is provided by the internal locking mechanism in each screw head which expands each screw head into engagement with the rounded seat portion in the first locking position, decreasing the potential for the head to back out of the rounded seat portion. The third level of security is provided by plastic deformation of the seat material around the screw head, which immobilizes the head in the material in the second locking position.

Testing of PEEK Material

Sample plates of PEEK material were prepared and tested with bone screws to confirm the performance characteristics of PEEK material. In particular, samples were tested to determine installation torques required to lock the screws in the first and second locking conditions, respectively. The sample plates were further tested to determine the required forces to push the screws out of each locking position, referred to as "push-out forces." The screws were ABC2 bone screws manufactured by Aesculap Implant Systems, Inc. Tests were carried out in accordance with ASTM F 2193 "Standard Specifications and Test Methods for components Used in the Surgical Fixation of the Spinal Skeletal System" and ISO 6475 "Implant for Surgery—Metal bone screws with asymmetrical thread and spherical under-surface—Mechanical requirements and test methods."

The ABC2 screws were inserted into 2.8 mm diameter holes pre-drilled into taped (FJ825R) PEEK test blocks. The holes were taped to minimize friction between the screw and the insertion block. The insertion torque was noted for 1.0 Nm and 2.0 Nm. The torque meter used for tightening implants in all tests had an accuracy quoted by the manufacturer of +/−10%. The push out tests followed protocol based on ASTM F 2193 and ISO 6475. Test blocks were inverted with the screws oriented vertically and the tips of the screw shanks facing upwardly. Load was applied onto the tips of the screw shanks.

Three ABC2 screw constructs were used at each load level. Load was applied at a rate of 0.08 inches per minute (approximately 2 mm/min) during the push out tests. The load against deflection curves were plotted and the peak load noted. Two such plots appear in FIGS. 10 and 11, which will be discussed in detail below. For the Flexion-Extension moment and static axial torque gripping capacity tests, complete failure typically followed immediately after the maximum load was reached. The failure of the components were illustrated on the force displacement curves as drops in load. The peak loads recorded for each sample are summarized in Table 1, below.

TABLE 1

| Sample # | Peak Load (lbf) | Peak Load (N) |
| --- | --- | --- |
| 1 | 12.851 | 56.9344 |
| 2 | 12.626 | 56.0448 |
| 3 | 12.027 | 53.376 |
| 4 | 61.672 | 274.4416 |

Samples 1-3 contained screws that were tightened into the block by a torque of approximately 1 N-m. No visible plastic deformation of PEEK material was observed on these samples. Furthermore, the ABC2 screws were movable in the block in pivot motion, analogous to the first locking position. For these samples, the recorded push-out forces were between about 12 lbf to about 13 lbf. The screw in Sample 4 was tightened with torque in excess of 1 N-m. Visible deformation of PEEK material was observed on the underside of Sample 4, indicating that the ABC2 screw heads were immobilized in the block analogous to the second locking position. For Sample 4, the recorded push-out force was approximately 62 lbf.

Figure 10:
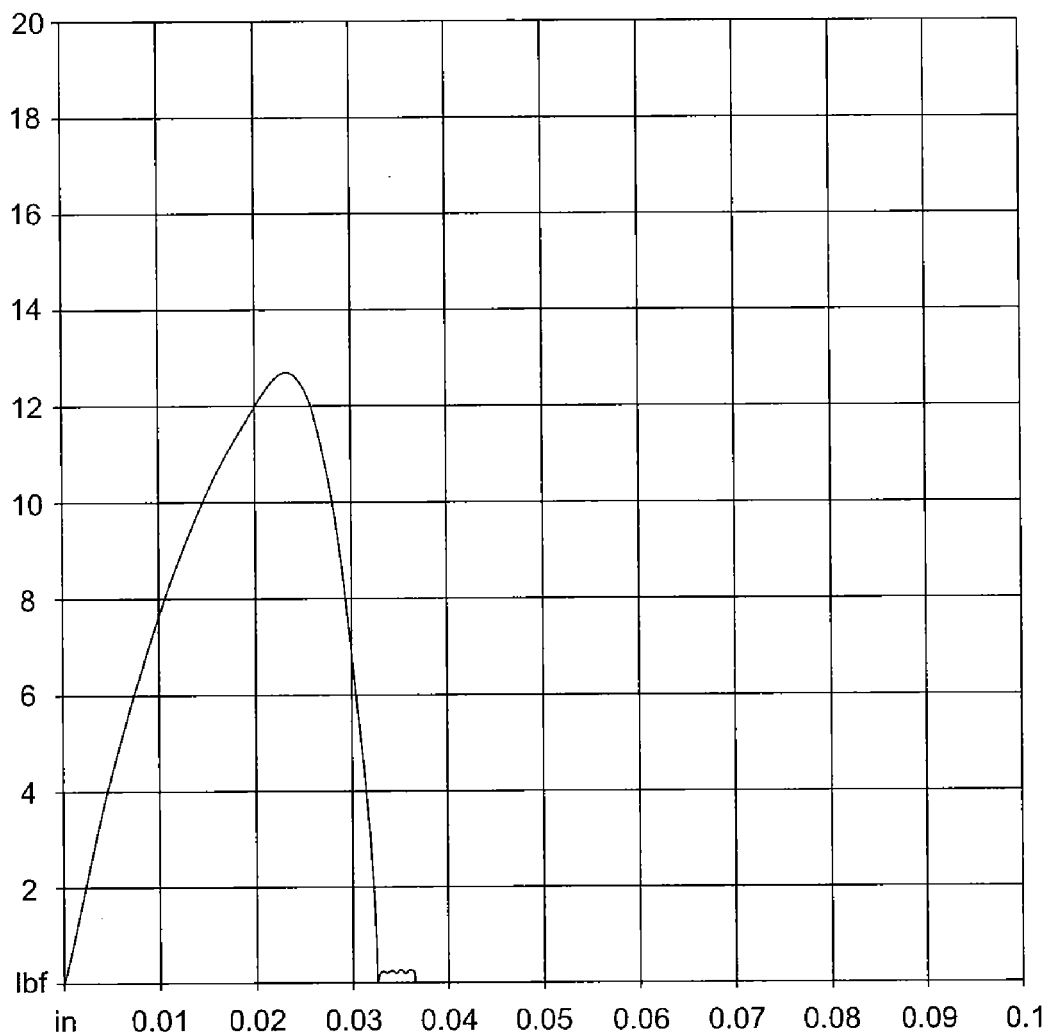
FIG. 10 is a first plot illustrating characteristics of locking mechanisms in accordance with the invention.

FIG. 10 is a plot that graphically illustrates the push-out resistance exhibited in Sample 1. The plot contains a large curve representing load versus deflection during the test. The vertical axis corresponds to the amount of axial load applied onto the screw, and the horizontal axis corresponds to deflection. Load was applied at a rate of approximately 0.08 in. per minute. The top of the curve represents the peak load recorded. The drop in load following the peak load represents failure of the construct under load. At the peak load of approximately 12.8 lbf, the internal locking mechanism in the screw head was overcome and the screw head was pushed completely out of the hole.

Figure 11:
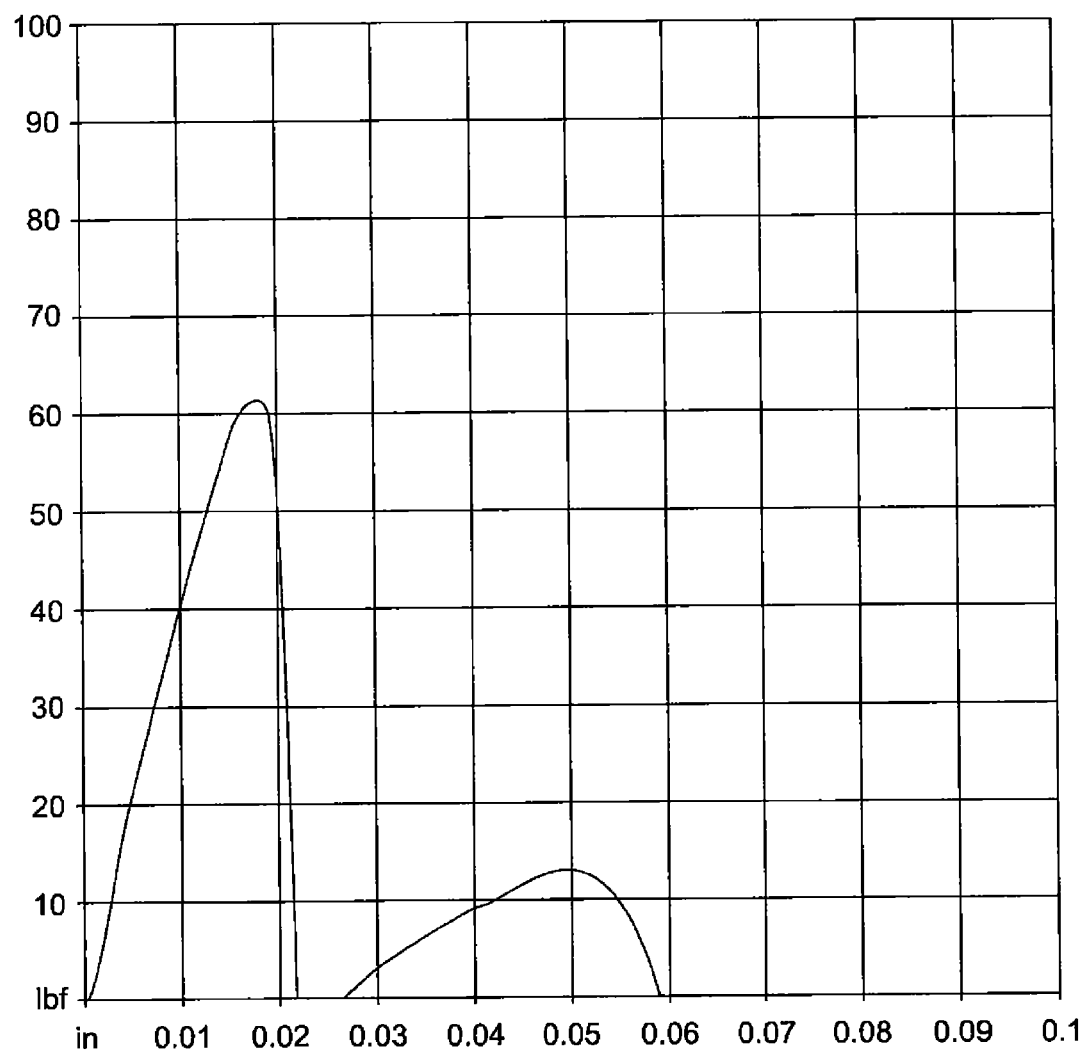
FIG. 11 is a second plot illustrating characteristics of locking mechanisms in accordance with the invention.

FIG. 11 is a plot similar to the plot in FIG. 10 that graphically illustrates the push-out resistance exhibited in Sample 4. The plot contains a large curve followed by a smaller curve. The large curve at the left of the plot represents load versus deflection as the screw head is forced out of the plastically deformed seat material from the second locking condition. The smaller curve on the right of the plot represents load versus deflection as the internal locking mechanism in the screw head was overcome, and the screw head was pushed completely out of the hole. At a first peak load of approximately 62 lbf, the screw head was forced out of the second locking condition, at which point the load dropped back down to 0 lbf. At a second peak load of approximately 12.8 lbf, the screw head was forced completely the hole.

The pair of curves in FIG. 11 graphically illustrate the second and third levels of security against push-out discussed above, assuming the assemblies of the present invention are set to constrained fixation. If force is applied to the screw that is sufficient to push the screw out of the second locking condition, the screw is still secured in the hole by the internal locking mechanism and the hole configuration. Therefore, the constrained fixation mode provides a primary locking mechanism and a secondary locking mechanism, each of which must be overcome before the screw completely fails.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the scope of the invention.

What is claimed:

1. An intervertebral implant comprising:
   a body for insertion between adjacent vertebrae;
   at least one anchor extending from the body for securing the body between said vertebrae;
   a carrier slidably displaceable in the body in a linear direction, wherein the at least one anchor is mounted in the carrier and movable with the carrier in the linear direction relative to the body;
   a linear motion control mechanism mounted in the body and operable to limit linear translation of the at least one anchor and carrier relative to the body; and
   a pivot control mechanism in the body operable to limit pivot motion of the at least one anchor relative to the body,
   wherein the at least one anchor comprises a rounded head and an elongated shank, and the carrier comprises a rounded seat, the head being pivotally displaceable against the seat, and the shank being displaceable in polyaxial motion relative to the carrier.

2. The intervertebral implant of claim 1, wherein the carrier comprises a locking pin displaceable relative to the carrier between a retracted position, in which the carrier is movable relative to the body, and an extended position, in which the carrier is in a fixed position relative to the body.

3. The intervertebral implant of claim 1, wherein the pivot control mechanism comprises a plastically deformable surface in the seat.

4. The intervertebral implant of claim 1, wherein the at least one anchor comprises a plurality of bone screws, and the pivot control mechanism comprises at least one plastically deformable seat.

5. The intervertebral implant of claim 4, wherein each bone screw comprises a plurality of segments that are radially displaceable between an expanded position and a contracted position.

6. The intervertebral implant of claim 4, wherein at least two screws are mounted in the carrier and movable in the linear direction relative to the body.

7. The intervertebral implant of claim 4, wherein the implant is configurable in a dynamic setting, in which the screws can translate in the linear direction and are pivotable relative to the body, a semi-constrained setting, in which the screws are fixed against translation in the linear direction and pivotable relative to the body, and a constrained setting, in which the screws are fixed against translation in the linear direction and fixed against pivot motion relative to the body.

8. An intervertebral implant comprising:
   a body for insertion between adjacent vertebrae;
   at least one anchor extending from the body for securing the body between said vertebrae, the at least one anchor comprising a head about which said at least one anchor is pivotable relative to the body;
   a carrier slidably displaceable in the body in a linear direction, wherein the at least one anchor is mounted in the carrier and movable in the linear direction relative to the body;
   a linear motion control mechanism connected with the head of the anchor and operable to limit linear translation of the anchor relative to the body; and
   a pivot control mechanism engaging the head of the at least one anchor and operable to limit pivot motion of the at least one anchor relative to the body,
   wherein the at least one anchor comprises a rounded head and an elongated shank, and the carrier comprises a rounded seat, the head on the at least one anchor being polyaxially displaceable against the seat, and the shank being displaceable in polyaxial motion relative to the carrier.

9. The intervertebral implant of claim 8, wherein the carrier comprises a locking pin displaceable relative to the carrier between a retracted position, in which the carrier is movable relative to the body, and an extended position, in which the carrier is in a fixed position relative to the body.

10. The intervertebral implant of claim 8, wherein the pivot control mechanism comprises a plastically deformable surface in the seat.

11. An intervertebral implant comprising:
    a body for insertion between adjacent vertebrae;
    at least one anchor extending from the body for securing the body between said vertebrae, said at least one anchor comprising a head about which the at least one anchor is pivotable relative to the body;

a carrier slidably displaceable in the body in a linear direction, wherein the head of the at least one anchor is mounted in the carrier and movable in the linear direction relative to the body;

a linear motion lock engaging the head of the at least one anchor and operable to limit linear translation of the at least one anchor relative to the body; and a pivot motion lock engaging the head of the at least one anchor and operable to limit pivot motion of the at least one anchor relative to the body, wherein the carrier comprises a rounded seat, and the head on the at least one anchor is polyaxially displaceable against the seat, the shank being displaceable in polyaxial motion relative to the carrier.

12. The intervertebral implant of claim 11, wherein the carrier comprises a locking pin displaceable relative to the carrier between a retracted position, in which the carrier is movable relative to the body, and an extended position, in which the carrier is in a fixed position relative to the body.

13. The intervertebral implant of claim 11, wherein the pivot control mechanism comprises a plastically deformable surface surrounding a portion of the head on the at least one anchor.

14. The intervertebral implant of claim 11, wherein the implant is configurable in a dynamic setting, in which the at least one anchor can translate in the linear direction and is pivotable relative to the body, a semi-constrained setting, in which the at least one anchor is fixed against translation in the linear direction and pivotable relative to the body, and a constrained setting, in which the at least one anchor is fixed against translation in the linear direction and fixed against pivot motion relative to the body.

15. An intervertebral implant comprising:
 a body for insertion between adjacent vertebrae, the body comprising a first screw hole;
 a first anchor extending through the first screw hole in the body for securing the body between said vertebrae;
 a carrier slidably displaceable in the body in a linear direction, the carrier comprising a second screw hole;
 a second anchor extending through the second screw hole for securing the body between said vertebrae, the second anchor moveable with the carrier in the linear direction relative to the first anchor and body; and
 a linear motion control mechanism mounted in the body and operable to control the amount of movement of the second anchor and carrier in the linear direction relative to the first anchor and body.

* * * * *